(12) United States Patent
Kumaran et al.

(10) Patent No.: US 10,502,677 B2
(45) Date of Patent: Dec. 10, 2019

(54) DETECTION OF CORROSION RATES IN PROCESSING PIPES AND VESSELS

(71) Applicants: Krishnan Kumaran, Raritan, NJ (US); Alan Mark Schilowitz, Highland Park, NJ (US); Henry Alan Wolf, Morris Plains, NJ (US)

(72) Inventors: Krishnan Kumaran, Raritan, NJ (US); Alan Mark Schilowitz, Highland Park, NJ (US); Henry Alan Wolf, Morris Plains, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 495 days.

(21) Appl. No.: 14/503,508

(22) Filed: Oct. 1, 2014

(65) Prior Publication Data
US 2015/0106036 A1    Apr. 16, 2015

Related U.S. Application Data

(60) Provisional application No. 61/890,370, filed on Oct. 14, 2013.

(51) Int. Cl.
*G01N 19/00* (2006.01)
*G01N 17/04* (2006.01)
(Continued)

(52) U.S. Cl.
CPC .......... *G01N 19/00* (2013.01); *G01N 17/04* (2013.01); *G01N 29/022* (2013.01);
(Continued)

(58) Field of Classification Search
CPC ........ G01N 17/04; G01N 19/00; G01N 27/04; G01N 29/022; G01N 29/036; G01N 2291/0427
See application file for complete search history.

(56) References Cited

U.S. PATENT DOCUMENTS 6,047,241 A     4/2000  Sparago
6,521,080 B2*   2/2003  Balasubramhanya ......................
                                        G01N 21/274
                                        118/723 E (Continued)

FOREIGN PATENT DOCUMENTS

WO       2011152970 A1    12/2011

OTHER PUBLICATIONS

PCT Application No. PCT/US2014/058722, Communication from the International Searching Authority, Form PCT/ISA/220, dated Dec. 23, 2014.

(Continued)

*Primary Examiner* — Judy Nguyen
*Assistant Examiner* — Leo T Hinze
(74) *Attorney, Agent, or Firm* — Andrew T. Ward; Glenn T. Barrett

(57) ABSTRACT

For a monitored corrosion sensor, such as a sensor based on one or more mechanical oscillators disposed in a fluid flow, one or more values are measured over time. The values can be measured at a desired frequency, such as a once per second, once per minute, or another convenient frequency. The measured data can then be analyzed as a time series. The goal of the analysis is to identify variations in the time series data that are sufficiently unexpected relative to the prior behavior of the time series within a given time window. The identified variations can then, for example, be excluded from consideration when determining a corrosion-related value for the sensor.

13 Claims, 7 Drawing Sheets

Corrosion Measurement Using a Reference Fork

(51) Int. Cl.
*G01N 29/02* (2006.01)
*G01N 29/036* (2006.01)
*G01N 29/30* (2006.01)

(52) U.S. Cl.
CPC .......... *G01N 29/036* (2013.01); *G01N 29/30* (2013.01); *G01N 2291/0258* (2013.01); *G01N 2291/0427* (2013.01)

(56) References Cited

U.S. PATENT DOCUMENTS

| | | | |
|---|---|---|---|
| 7,085,675 B2 * | 8/2006 | Wegerich | G05B 23/024 |
| | | | 702/181 |
| 7,334,452 B2 * | 2/2008 | Matsiev | G01H 13/00 |
| | | | 73/24.06 |
| 7,598,820 B2 | 10/2009 | Alvarez et al. | |
| 7,681,449 B2 | 3/2010 | Wolf et al. | |
| 7,721,605 B2 * | 5/2010 | Wolf | G01N 17/04 |
| | | | 73/579 |
| 7,731,605 B2 | 6/2010 | Melanson et al. | |
| 7,827,006 B2 * | 11/2010 | Miller | G05B 23/024 |
| | | | 702/183 |
| 2006/0218996 A1 * | 10/2006 | Matsiev | F02D 41/021 |
| | | | 73/64.53 |
| 2010/0275689 A1 | 11/2010 | Wolf et al. | |
| 2010/0324852 A1 | 12/2010 | Wolf et al. | |
| 2012/0123756 A1 * | 5/2012 | Wang | E21B 44/00 |
| | | | 703/2 |

* cited by examiner

US 10,502,677 B2

DETECTION OF CORROSION RATES IN PROCESSING PIPES AND VESSELS

CROSS REFERENCE TO RELATED APPLICATION

This application relates and claims priority to U.S. Provisional Patent Application No. 61/890,370 filed on Oct. 14, 2014.

FIELD OF THE INVENTION

This invention is directed to improved detection and/or estimation of corrosion within refinery pipelines.

BACKGROUND

Corrosion is a significant problem in petroleum refineries and other industrial plants which process corrosive materials. Corrosion can cause deterioration of valves, gauges and other equipment. Corrosion can also cause leaks with large environmental and financial costs.

Corrosive species involved in the production and processing of crude oil and hydrocarbons may cause metal-loss corrosion of production, transfer, storage, and processing equipment. Erosive species typically involve fluid and/or solids turbulence causing metal loss from mechanical actions rather than chemical. For example, these corrosive/erosive species may be hydrocarbon, hydrocarbon containing materials, or aqueous, or combinations thereof. Moreover, streams may be single or multi-phase (solids, liquids, gases).

Various sensors can be used to monitor corrosion. In most cases, a sensor detects corrosion based on a correlation between a measurable property of a sensor, such as resonant frequency, and the corrosion rate. Typically a sensor will be connected to a display which can be monitored to determine the relative corrosion rate which has occurred on the sensor, and therefore potentially has occurred in an associated system. The most common areas of corrosion concern in a reaction system are at the interior wall of a pipe or vessel. In some cases, internal vessel components such as baffles or cyclones may also be subject to corrosion and/or erosion.

An important challenge in obtaining reliable corrosion estimates using a sensor disposed in a corrosive process fluid environment arises from the frequent changes in the physical properties of the fluid—such as temperature and viscosity—which alter the measured values for a sensor independent of corrosion. For example, for a sensor using a mechanical oscillator, changes in the resonant frequency that are unrelated to corrosion can be difficult to distinguish from the corrosion-related changes. This can lead to complications in attempting to determine a corrosion rate based on analysis of measured values related to a corrosion sensor. For a sensor using electrical resistance, changes in the element resistance that are unrelated to corrosion are similarly problematic.

SUMMARY OF THE PREFERRED EMBODIMENTS OF THE INVENTION

In an aspect, a method for determining a corrosion rate for a sensor in a fluid flow in a corrosive or erosive environment is provided. The method includes exciting a mechanical oscillator disposed in a fluid flow; monitoring the mechanical oscillator to obtain a plurality of sampling values at a plurality of times, a sampling value comprising at least one of a resonant frequency f and a quality factor Q; forming pattern window vectors having a first window size based on the plurality of sampling values, each pattern window vector being associated with a time from the plurality of times; determining residue values for the pattern window vectors at the plurality of times based on a mean vector and a variance, the mean vector and the variance for a pattern window vector associated with a time being based on at least a portion of the pattern window vectors; identifying one or more residue values greater than a threshold value; excluding sampling values from the plurality of sampling values that correspond to times associated with the one or more identified residue values; determining a resonant frequency decrease in the mechanical oscillator based on sampling values from the plurality of sampling values that are different from the excluded sampling values; and determining a corrosion rate based on the determined resonant frequency decrease.

In another aspect, a method for determining a corrosion rate for a sensor in a fluid flow in a corrosive or erosive environment is provided. The method includes exciting a mechanical oscillator disposed in a fluid flow; monitoring the mechanical oscillator to obtain a plurality of sampling values at a plurality of times, a sampling value comprising at least one of a resonant frequency f and a quality factor Q; forming pattern window vectors having a first window size based on the sampling values; selecting a memory value $\mu$, where $1/\mu$ is greater than the first window size; determining residue values for the pattern window vectors at the plurality of times based on the selected memory value, a moving mean vector, and a moving variance, the moving mean vector and the moving variance for a pattern vector associated with a time being based on at least a portion of the pattern window vectors; identifying one or more residue values greater than a threshold value; excluding sampling values from the plurality of sampling values that correspond to times associated with the one or more identified residue values; determining a resonant frequency decrease in the mechanical oscillator based on sampling values from the plurality of sampling values that are different from the excluded sampling values; and determining a corrosion rate based on the determined resonant frequency decrease.

In still another aspect, a method for determining a corrosion rate for a sensor in a fluid flow in a corrosive or erosive environment is provided. The method includes monitoring a corrosion sensor disposed in a fluid flow to obtain a plurality of sampling values at a plurality of times, a sampling value comprising one or more measured values of the monitored sensor, forming pattern window vectors having a first window size based on the plurality of sampling values, each pattern window vector being associated with a time from the plurality of times; determining residue values for the pattern window vectors at the plurality of times based on a mean vector and a variance, the mean vector and the variance for a pattern window vector associated with a time being based on at least a portion of the pattern window vectors; identifying one or more residue values greater than a threshold value; excluding sampling values from the plurality of sampling values that correspond to times associated with the one or more identified residue values; determining a change in at least one measured value of the monitored sensor based on sampling values from the plurality of sampling values that are different from the excluded sampling values; and determining a corrosion rate based on the determined change in the at least one measured value. Optionally, the monitored corrosion sensor can comprise an electrical resistance probe, a mechanical oscillator, or a combination thereof.

In yet another aspect, a method for determining a corrosion rate for a sensor in a fluid flow in a corrosive or erosive environment is provided. The method includes determining a change in at least one measured value of the monitored sensor based on sampling values from the plurality of sampling values that are different from the excluded sampling values; and determining a corrosion rate based on the determined change in the at least one measured value forming pattern window vectors having a first window size based on the sampling values; selecting a memory value $\mu$, where $1/\mu$ is greater than the first window size; determining residue values for the pattern window vectors at the plurality of times based on the selected memory value, a moving mean vector, and a moving variance, the moving mean vector and the moving variance for a pattern vector associated with a time being based on at least a portion of the pattern window vectors; identifying one or more residue values greater than a threshold value; excluding sampling values from the plurality of sampling values that correspond to times associated with the one or more identified residue values; determining a change in at least one measured value of the monitored sensor based on sampling values from the plurality of sampling values that are different from the excluded sampling values; and determining a corrosion rate based on the determined change in the at least one measured value. Optionally, the monitored corrosion sensor can comprise an electrical resistance probe, a mechanical oscillator, or a combination thereof.

BRIEF DESCRIPTION OF THE DRAWINGS

The attached Figures represent alternative embodiments of the overall invention, as well as comparative examples. The Figures pertaining to the invention are intended to be viewed as exemplary embodiments within the scope of the overall invention as claimed.

DETAILED DESCRIPTION

Overview

Figure 1:
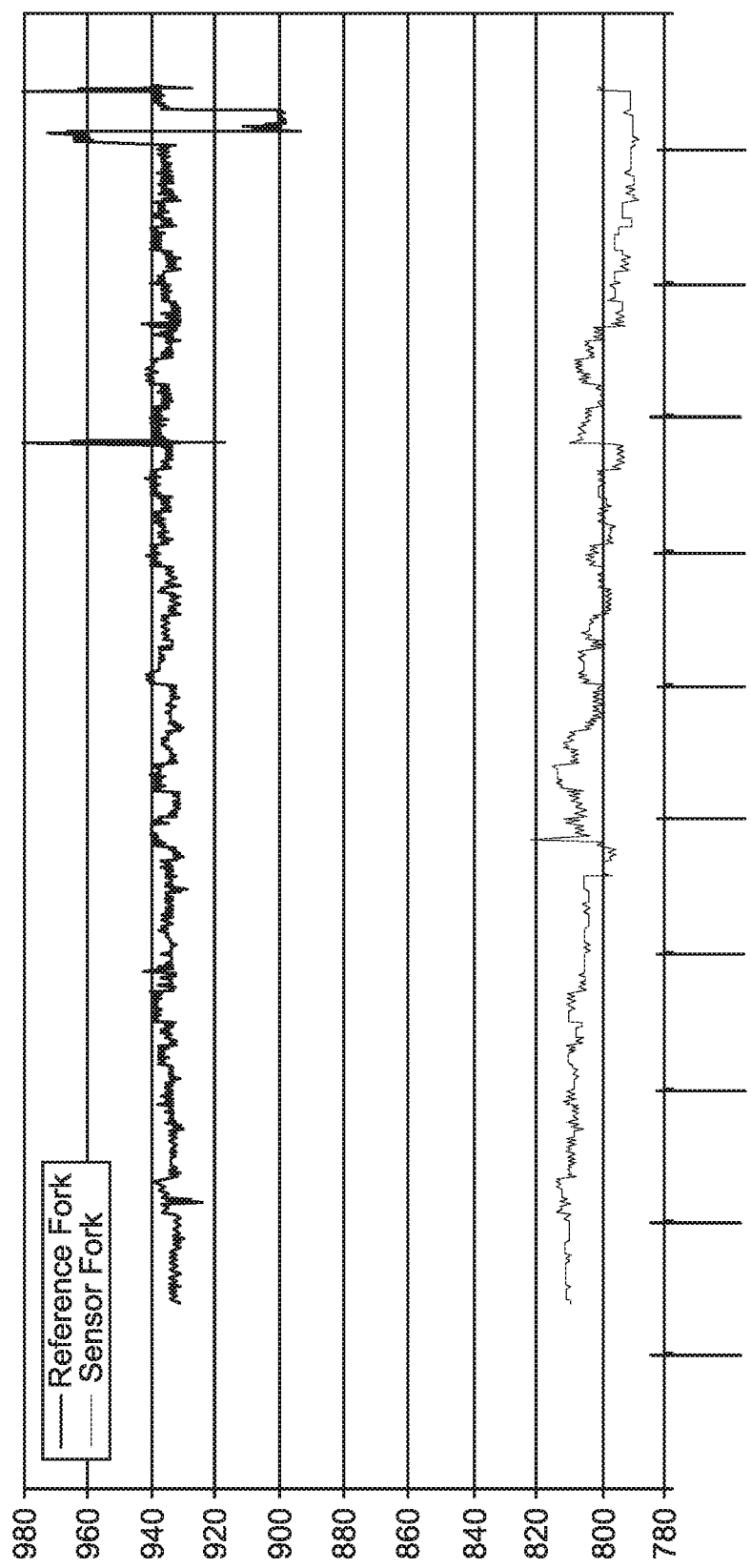
FIGS. 1-5 show examples of analysis of frequency measurements of mechanical oscillators in a fluid flow.

In some aspects, the invention relates to a metal loss measurement system for the detection of corrosion and for measuring the rate of metal mass loss from a corrosion sensor, such as a mechanical corrosion sensor. Such a system can be used, for example, measure a corrosion rate for the sensor, thereby allowing an estimate of the corrosion and/or erosion rate within a processing environment that is exposed to a process fluid. The invention may be applied generally to the detection of metal-loss by corrosion and/or erosion species in single or multiphase fluids. In particular, the present invention relates to the on-stream detection of metal-loss corrosion and/or erosion during an industrial production process. The actual service environment may be aqueous, solid (such as solids suspended in a liquid), hydrocarbon, chemical or a combination thereof.

In various aspects, one potential goal of using a corrosion sensor is to reduce or minimize the amount of lost processing time for a reaction system due to both scheduled maintenance as well as unexpected shutdown events. In general, unexpected shutdowns of a processing system due to corrosive failure of a portion of the system are not desirable. In order to avoid unexpected shutdowns, scheduled shutdown events can be performed. In the absence of monitoring, the frequency of scheduled shutdown events must be sufficiently high so that even an unexpectedly high corrosion rate will not lead to failure of a portion of the reaction system prior to the scheduled shutdown event. Monitoring the corrosion within the reaction system can increase the time between scheduled shutdown events by allowing the actual corrosion rate to be monitored. However, when using conventional corrosion sensors, difficulties in obtaining accurate sensor data can limit the confidence in the sensor measurements, meaning that scheduled shutdown events will still occur more frequently than is desired. If the analysis of the sensor data can be improved to allow increased confidence in the measured corrosion rate, the time between scheduled shutdowns can be increased.

In a corrosive or erosive process fluid environment, a corrosion sensor may generate two types of data that do not relate to corrosion due to the process fluid. One type of data corresponds to data indicating deposition on the sensor. For example, a hydrocarbon or petroleum fluid environment can lead to deposition of iron sulfide and/or other solids (sometimes referred to as scale deposition) on a sensor. For a mechanical sensor, deposition of additional material can alter the physical properties of the sensor, such as the resonant frequency. For example, if corrosion of the sensor typically leads to a decrease in resonant frequency, deposition can instead lead to an increase in resonant frequency. Such an increase in resonant frequency, when measured, corresponds to "unphysical" data that is not helpful in determining the corrosion rate. As another example, for a corrosion sensor based on electrical resistance, some deposited materials (such as iron sulfide) can be conductive and/or semiconductive, leading to a decrease in the resistance of the sensor, when an increase in resistance is expected as an indicator of corrosion.

In these types of situations, data that is "unphysical", or clearly indicative of a process other than corrosion, can be excluded. In the case of a mechanical oscillator, such "unphysical" data can be identified based on the change in slope of the resonant frequency curve. When corrosion leads to a decrease in resonant frequency, the slope of the resonant frequency over time should be negative. When the slope becomes positive for a period of time due to deposition, the data during that time period can be excluded. This allows the corrosion rate to be determined using only the portions of data that match corrosion behavior.

Unfortunately, some types of events that are not related to corrosion or erosion are more difficult to exclude. For example, changes in the temperature, viscosity, or pressure within the process fluid may lead to (possibly temporary) changes in the resonant frequency that do not reflect loss of material from the corrosion sensor. Such changes in the resonant frequency due to other variables may still provide a negative slope for the resonant frequency over time, but are not representative of the true corrosion rate. Likewise, for electrical resistance probes, changes in process temperature can cause a resistance change in the corrodible element that is not related to corrosion. The windowed statistical analysis described herein provides a method for identifying and excluding these data anomalies to further improve the calculation of a corrosion rate for a sensor.

In various aspects, the measurement of a corrosion rate for a corrosion sensor can be enhanced based on use of methods that can automatically extract, and thus exclude from analysis, anomalous changes in the resonant frequency of a mechanical oscillator that are not connected with corrosion and/or erosion of a corrosion sensor disposed in a fluid flow.

Such effects can occur due to temporary issues with uncompensated noise interference on the sensors, transient remnant effects from past anomalous events, or due to other factors. A benefit of being able to exclude anomalous event data is that automatic determination of corrosion rate estimates can be improved. The improved estimates can be based on frequency data that takes into account recent data as well as historical data from the recent past.

As an example, one or more mechanical corrosion sensors disposed in or otherwise exposed to a fluid flow in a process environment are monitored over time. The monitoring of the corrosion sensors can include, for example, measurement of the resonant frequency "f" of the corrosion sensor(s). Optionally, additional values can also be measured, such as the quality factor "Q" of the corrosion sensor(s). Optionally, at least one of the sensors can correspond to a reference sensor that is resistant to corrosion (such as non-corrodible) in the fluid flow. The behavior of the measured value(s) over time is analyzed using groupings or windows of data to identify anomalous features in the time-average values. For example, anomalous features can be identified based on a threshold value generated from the analysis. These anomalous features are then excluded from the data when determining the change in resonant frequency (and/or other measured values) of the sensor, and therefore are also excluded when determining the corrosion rate for the sensor within the process environment that is exposed to the fluid flow. This can facilitate and improve automatic determination of corrosion rates, so that the reaction system can remain in operation with reduced concern of an unexpected failure in a reaction system structure such as a pipe or a reactor wall.

The anomalous features can be identified using a windowed statistical analysis technique. For a monitored corrosion sensor, the value of one or more sensor characteristics over time is measured. For example, the value of the sensor characteristics can be measured periodically, such as by measuring at a desired sampling frequency. Examples of suitable sampling frequencies include once per second, once per minute, or another convenient sampling frequency. The measured data can then be analyzed as a time series. The goal of the analysis is to identify variations in the time series data that are sufficiently unexpected relative to the prior behavior of the time series within a given time window. By analyzing windows of data instead of individual data points, time-dependent patterns can be identified in the data. Anomalous features can then be identified based on detection of unusual patters over a time window. Because the anomalous features are detected based on a time window, an anomalous feature can be detected even though none of the individual data points appear unusual by themselves. It is noted that the sampling frequency will usually be unrelated to any characteristic frequencies of the sensor, such as the resonant frequency of a mechanical oscillator that is part of the sensor.

After removal or exclusion of data that is anomalous relative to the expected corrosion behavior of the mechanical oscillator, analysis of the changes in the measured values over time should be facilitated. In particular, fewer outlier points should remain, allowing for an improved fit of a functional form to estimate the rate of change in, for example, resonant frequency over time. The rate of change in resonant frequency over time can then be used to determine a corresponding corrosion rate for the corrosion sensor.

Another option is to use an electrical resistance probe as a corrosion sensor. For electrical resistance probes, corrosion of the probe is measured based on changes in the resistivity of the probe. Corrosion of the probe leads to loss of cross-section for the probe, resulting in a corresponding increase in resistivity. The windowed analysis technique can be used in a similar manner for an electrical resistance probe in order to exclude anomalous data when determining the rate of corrosion for the probe. It is noted that deposition from the process fluid environment can lead to a decrease in resistivity due to deposition of a conducting or semiconducting material, such as iron sulfides. More generally, the windowed analysis technique can be used with any type of corrosion probe where a time series of a measurable quantity for the probe can be correlated with a corrosion rate using a predictable functional form, such as a polynomial functional form.

After determining the change in a measured parameter over time, such as the resonant frequency of a sensor based on a mechanical oscillator, the change in resonant frequency can be used to calculate a corrosion rate for the sensor. In some aspects, the corrosion rate can be correlated with the change in resonant frequency based on prior fitting of a functional form for the correlation. For example, for sufficiently small amounts of mass loss from a mechanical oscillator (or from conductive element in an electrical resistance sensor), a linear functional form may be adequate to fit the change in measured property with the change in mass of the sensor. More generally, a polynomial data fit can be determined based on prior test data to provide a correlation between change in a measured property of a sensor with a change in mass over time. Of course, if desired other types of functional forms can be used for the data fit as well, such as exponential functions, logarithmic functions, or any other convenient type of function or combination of functions.

Definitions

In order to clarify the description of the invention, the following definitions are provided. The following definitions should be applied throughout the description herein unless otherwise specified.

In various aspects, one or more sensors can be used that consist of or otherwise include a mechanical oscillator. In the most general embodiment, the oscillator has a vibrating element such as tuning fork tines or a rod. As examples, the cross-sectional shape of the tines or rod may be circular, rectangular, or as otherwise determined by finite element analysis described subsequently. These vibrating elements are attached to a diaphragm. The vibrating elements (e.g. tines or rod) have regions that respond to exposure to a fluid flow of a process or service fluid at different corrosion rates. The vibrating element includes a base and a tip region. The oscillator has a resonance frequency, f, and the quality factor associated with the resonance, Q. The resonance factor Q is inversely proportional to the total system damping. The mechanical excitation may be provided by the flow of the process or service fluid or by active excitation at the diaphragm. As an example, this active excitation may be provided by a piezoceramic driver. When driven by an external energy source, such as a piezoceramic driver, it is not required to continuously provide the excitation. The excitation can be applied at the times it is desired to interrogate the corrosion sensor. Preferably, the regions are selected so that the regions with higher corrosion rates will lead to a reduction in the resonant frequency for the oscillator as corrosion increases. For example, a region on the base of a tuning fork can have a greater corrosion rate in a fluid flow than a region on a tine of the tuning fork.

It is well established in the literature that a lightly damped harmonic oscillator with single degree of freedom can be mathematically expressed by a second order differential equation. In general, the resonance frequency can be represented by $f_0=(1/2\pi)*\sqrt{(k/m)}$ and the quality factor, Q, can be represented by $Q=(1/c)*\sqrt{(k*m)}$, where m is the system mass, k is the system stiffness, c is the velocity dependent damping, $f_0$ is the resonance frequency, and Q is the quality factor (a measure of the system damping and energy dissipation). There is an implicit assumption that the damping is light so that the mechanical resonance can be observed. Based on the changes in $f_0$ (and optionally Q) over time, changes in mass of the oscillator can be identified which allow for prediction of corrosion rates.

In some aspects of the invention, reference is made to performing analysis using data vectors. Unless otherwise specified, in this discussion the term "vector" is explicitly defined to include multi-dimensional vectors, which could also be referred to as matrices. Similarly, it is noted that a matrix can potentially have only a single row or column of values. As a result, unless otherwise specified, the terms vector and matrix can be used interchangeably herein. As an example, a 1-dimensional vector can be represented as a matrix that has a single row or a single column. A 2-dimensional vector can correspond to a matrix that has both a plurality of rows and a plurality of columns.

In various aspects, the corrosion rates of sensors disposed in a process fluid will be referred to. Unless otherwise specified, it is understood that a corrosion rate refers to any rate of loss of material from a sensor. Thus, as used herein, a corrosion rate can represent loss of material from a sensor due to corrosion, erosion, or by any other convenient mechanism.

In various aspects, a corrosion-related value for a sensor will be referred to. A corrosion-related value is any value that can be used to determine and/or infer an amount of corrosion for a sensor. A corrosion rate is one example of a corrosion-related value. More generally, a measured value for a sensor over time, or a value that can be derived from the time measurements of the sensor can also be a corrosion-related value. For example, for a mechanical oscillator, the resonant frequency over time is a value that can be tracked. Even for a mechanical oscillator with no prior calibration relative to an amount of corrosion, the rate of change in the resonant frequency can be observed. If the rate of change in the resonant frequency over time increases or decreases, that can correspond to a corrosion-related value, as such a rate of change at least qualitatively indicates a change in the corrosion rate.

Corrosion Detection Using Mechanical Oscillators

In some aspects, a single tuning fork with two regions of differing corrosion resistance is used. Regions of differing corrosion resistance include the case where one of the regions does not corrode at all. In a preferred embodiment, both regions are subjected simultaneously to the corrosive environment. In other aspects, a second non-corrodible tuning fork is used as a reference fork to provide a corrosion sensor based on multiple mechanical oscillators. For both types of corrosion sensors (single oscillator and multiple oscillator), the corrosion rate can be determined based on the change in resonant frequency over time, or both resonance frequency and Q can be used in the determination of corrosion and/or erosion.

Figure 6:
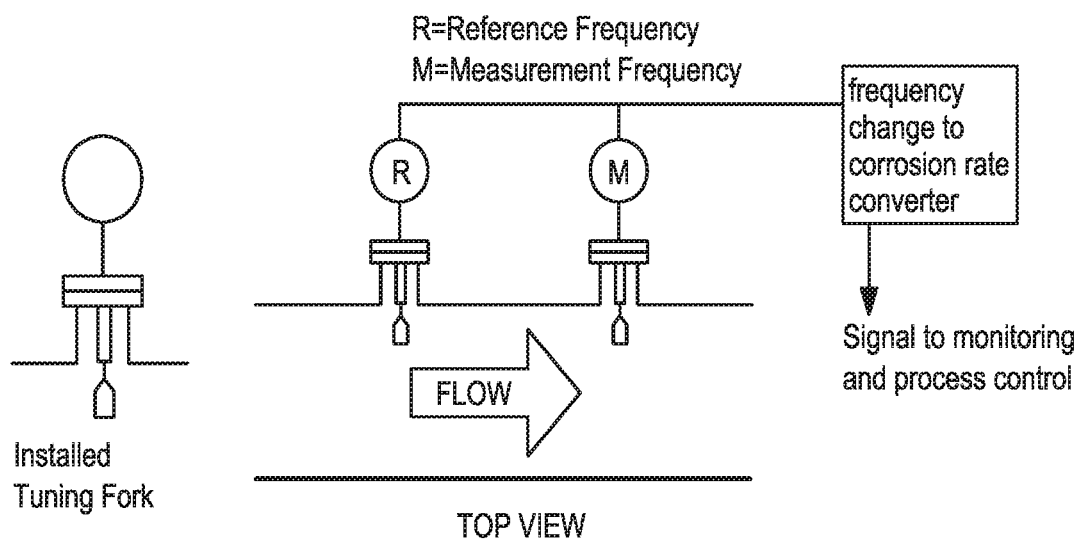
FIG. 6 shows an example of a corrosion sensor.

In some aspects, at least two oscillators can be used, with one of the oscillators being a reference oscillator composed of a non-corrodible (such as highly corrosion resistant) material. FIG. 6 shows an example of a system for measuring a corrosion rate within a system containing a fluid flow, such as a pipe or another volume that is surrounded by a pressure containment boundary. The fully compatible mechanical oscillator (non-corrodible) is used as a reference measurement, as it can be used to track process fluid changes (such as viscosity, density and temperature) that would influence the observed changes in the oscillator not attributable to corrosion. The second oscillator (with a portion of the material being affected by the process fluid, as in the case of corrosion) experiences the same changes, but in addition it would experience the changes due to the corrosion caused by the fluid. This difference in behavior is then translated into a metal loss rate for the material at the process conditions, and is used to monitor the corrosion/erosion rate to determine safe operation, effectiveness of corrosion inhibitors, inhibitor dosage control and/or predicting remaining wall in piping and vessels. Other embodiments are also possible and described. To minimize the impact of corrosion scale deposition, the corrodible oscillator can be configured using elements with different corrosion rates as describe in the single oscillator embodiment.

This embodiment of using two oscillators can potentially be used to account for the effects of any corrosion scale or fouling deposition that is not excluded by the data analysis method. The data from the two oscillators can be combined in any convenient fashion, such as by subtracting the data of one oscillator from the other oscillator or by using a ratio of the data from the two oscillators. The approach also has the benefit of directly accounting for minor variations in the service fluid impacting temperature, density, and viscosity that are not excluded by the data analysis method. In the absence of any corrosion, the change in resonance parameters of both oscillators can be directly attributable to parameters other than mass loss (e.g. deposition, density, etc.). Any divergence between the resonance parameters of the two oscillators is attributable to mass loss in the oscillator fabricated with the corrodible components. If the two oscillator approach is to be deployed, the effects of corrosion scale deposition can be minimized using an oscillator design that involves using multiple corrodible elements. There are two reasons the multiple tuning fork approach may be less desirable than the single oscillator approach of the preferred embodiments. One reason is the cost of materials and installation of the second oscillator. The other reason is the assumption that both oscillators will be exposed to the same corrosion and process environments.

Figure 7:
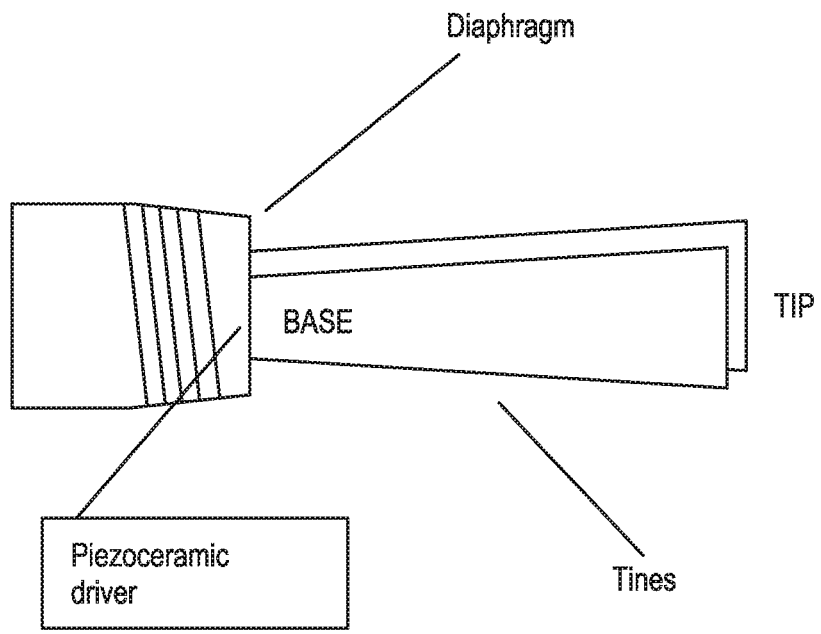
FIGS. 7 and 8 show examples of configurations for a mechanical oscillator.
Figure 8:
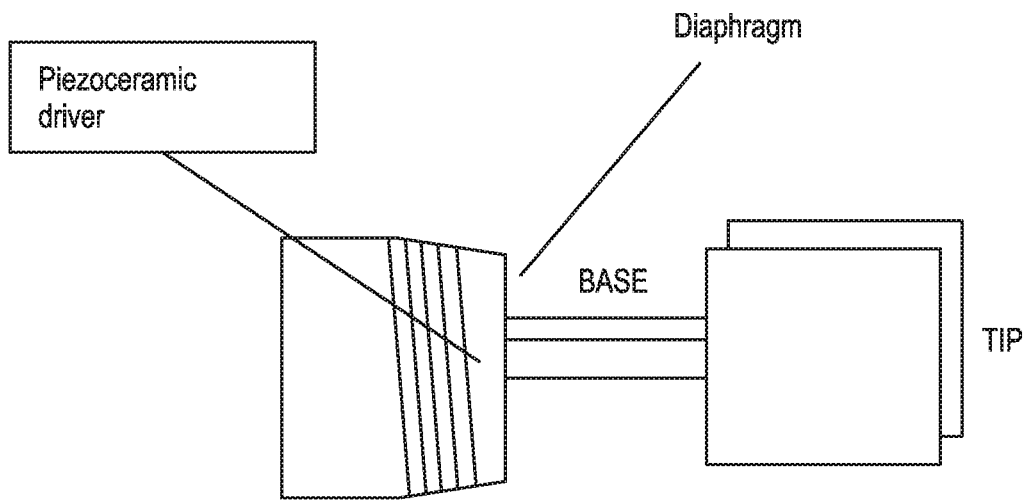

FIG. 7 illustrates the tines of an example of a commercial tuning fork level sensor (FORK A). The figure identifies a "diaphragm", "tip" and "base" portion of the tuning fork. FIG. 8 shows a similar plan view of another commercial tuning fork level sensor (FORK B). The tine shape of FORKS A and B are different. The tine shape can have an impact on the sensitivity to measure corrosion. The vibratory excitation for tuning FORKS A and B is achieved with a piezoceramic driver attached to the diaphragm.

Data Monitoring and Accumulation for Reaction Systems

In various aspects of the invention, one or more values for a corrosion sensor (comprising one or more mechanical oscillators) can be measured on a periodic basis. Values that can routinely be measured include the resonant frequency $f_0$ and optionally the quality factor Q. Optionally but preferably, just the resonant frequency of the mechanical oscillator(s) can be used to determine a corrosion rate.

The sampling rate for measuring a value can be any convenient rate. In some aspects, the sampling rate can be selected based on an expected relevant time scale for the measured value. Thus, the sampling rate can be on the order of milliseconds, seconds, minutes, or hours, depending on the nature of the monitored process. It is noted that the measurement rate for measuring a mechanical oscillator does not have to be the same as the sampling rate for use in data analysis. For example, the resonant frequency can be measured once a second, but the data analysis may use only one out of every two measured values. More generally, any convenient relationship between the measurement rate and the sampling rate can be used. Additionally, if the sampling rate is lower than the measurement rate, averaging or blending of the measured values to generate average sample values can also be performed.

It is noted that for each measurement and/or sampling value, a plurality of values can actually be collected. In this type of embodiment, at each sampling point, more than one measurement value is available. For example, both a resonant frequency and a quality factor can be measured for an oscillator that is being monitored. This would result in each sampling point corresponding to a vector containing two values.

Anomaly Detection to Identify Corrosion

The following techniques can be referred to, in part or collectively, as windowed statistical analysis. In various aspects of the invention, either before or after selecting the measurement rate and/or sampling rate, time windows for performing analysis on the data can also be selected. One type of time window can be a "pattern window". The pattern window describes the number of data points that are considered together as a grouping. For example, if the pattern window has a size of 10 data points, when the measurement data is analyzed, the data can be used as groups of 10 data points. Preferably, the pattern windows for a data set can overlap. For example, for a pattern window of 8 data points, a first window can contain measurements 1-8, while the next window can correspond to measurements 2-9. By using the data set within a pattern window as the smallest chunk of data that is analyzed, the analysis can capture more than just the instantaneous states of a reaction system. Instead of focusing just on individual data points, use of pattern windows allows short term behavior (such as process dynamics) of a system to also be captured.

The size of the pattern window can be any convenient size. The size for the pattern window can be selected based on several factors. A larger pattern window size is beneficial for detecting anomalous patterns that are expressed over a larger number of data points. However, use of a larger pattern window can reduce the speed with which a shorter anomaly is identified. Suitable pattern window sizes can be at least about 5 sampling points, such as at least about 8 sampling points or at least about 10 sampling points. Additionally or alternately, the pattern window size can be as large as desired. From a practical standpoint, the pattern window size can be about 50 sampling points or less, such as about 25 sampling points or less, or about 20 sampling points or less.

Another type of time window is the sampling or memory window. The sampling or memory window should be substantially larger than the pattern window. The sampling window corresponds to the number of measurements that are considered in determining whether a subset of the measurements (such as the pattern window) corresponds to unusual or anomalous data. The sampling window can correspond to an explicit number of pattern windows that are considered when calculating properties for a time series of data. Alternatively, the sampling window can be approximated by using a weighting factor for blending a new pattern window vector into the existing analysis. By using a weighting factor, older pattern vectors become progressively less important in the accumulated data, which has an effect similar to having a fixed size for the sampling window.

In some preferred aspects of the invention, the size of the sampling window can be substantially larger than the size of the pattern window, such as having a sampling window that is at least about 5 times the size of the pattern window, or at least about 10 times the size of the pattern window, or at least about 20 times the size of the pattern window. One of the goals of the pattern window analysis can be to identify anomalous patterns in a data set. If the sampling window is not sufficiently large relative to the pattern window, the sampling window may not incorporate enough of the pattern history for a system. This can lead to, for example, false positives in identification of anomalous patterns when a common but infrequent pattern may be identified as anomalous. If a memory parameter $\mu$ is used instead of an explicit sampling window, the value of $\mu$ can be selected so that $1/\mu$ is substantially larger than the size of the pattern window. Depending on the aspect, a suitable value for $\mu$ can be about 0.1 or less, such as about 0.05 or less, or about 0.01 or less, or even about 0.001 or less.

In some aspects of the invention, data analysis can be performed using a plurality of sampling windows and/or pattern windows based on the same data. As described in more detail below, changing the size of the sampling window and/or pattern window can impact the types of anomalies that are detected. Additionally, changing the size of the sampling window and/or pattern window can impact how quickly an anomaly is detected.

After selecting a pattern window size and a sampling window size (or alternatively a sampling weighting factor), the analysis technique can be applied to the data. The analysis includes several steps which are repeated for each new measurement included in the analysis.

At the beginning of the analysis, an initial vector of values is formed for each measurement or data point. In the example below, data corresponding to a resonant frequency will be discussed, so the vector for each data point in the example will have a length of one. However, it is understood that the discussion below can equally apply to data point vectors of an arbitrary length, such as data point vectors comprising a plurality of data values.

The data point vectors for each data point can then be used to form pattern window vectors. The pattern window vectors have a width corresponding to the size of the data point vectors and a length corresponding to the pattern window size. In an example where the data point vectors correspond to frequency value, and where the pattern window is of size 10, the pattern window vector has a width of 1 and a length of 10. Such a pattern window vector corresponds to a one-dimensional vector, or a matrix corresponding to a single row or column.

For each new data point vector (i.e, each new measurement(s) point), a new pattern window vector is created. In the example of a single measured value and a pattern window of 10, a new vector is created by using values 1-9 from the prior pattern window vector as values 2-10 for the new vector. Element 1 of the new vector corresponds to the new measured value(s). Element 10 from the prior vector is not directly used in forming the new vector. As additional data point vectors are obtained, additional pattern window vectors are formed. It is noted that for the first few data points, a sufficient number of data point vectors will not be available to form a pattern window vector. In order to initiate the process, a default set of data point vectors can be provided.

Equation (1) shows an example of using data point vectors x to form a plurality of pattern window vectors y. The plurality of pattern window vectors y shown in Equation (1) represent the number of pattern window vectors that are contained within a sampling window of window size $W_m$.

$$\{\underline{y}(W_p), \ldots \underline{y}(W_m + W_p - 1)\} \equiv \left\{ \begin{bmatrix} x(1) \\ x(2) \\ \vdots \\ x(W_p) \end{bmatrix}, \begin{bmatrix} x(2) \\ x(3) \\ \vdots \\ x(W_p + 1) \end{bmatrix}, \ldots, \begin{bmatrix} x(W_m) \\ x(W_m + 1) \\ \vdots \\ x(W_m + W_p - 1) \end{bmatrix} \right\} \quad (1)$$

In Equation (1), x(t) corresponds to the measurement value or values at time t. In equation (1), x(t) is shown as a single value for convenience, but it could also represent a plurality of measured values at the time t. $W_p$ corresponds to the size of the pattern window. $W_m$ corresponds to the sample window size. y[x(t)] corresponds to the pattern window vector for each time t.

Formation of the pattern window vectors can allow for analysis of the data point vectors based on groups of the data point vectors, as opposed to analyzing individual data points. Using Equation (1), values such as the mean, second moment, and variance could be directly calculated at each time "t" based on the preceding pattern vectors within the sampling window. Alternatively, rather than explicitly performing a calculation on the collection of pattern vectors in a sampling window at each time t, the sampling window can be approximated using a weighting factor μ. This results in calculation of a moving mean, moving second moment, and moving variance. Equations (2)-(5) correspond to the transformations that enable determination of a moving mean, moving second moment, and moving variance based on pattern window vectors in order to identify unusual or anomalous behavior.

$$m(t) = \mu y(t) + (1-\mu)m(t-1); \; m(1) = y(1) \quad (2)$$

$$\Lambda(t) = \mu y(t)[y(t)]^T + (1-\mu)\Lambda(t-1); \; \Lambda(1) = y(1)[y(1)]^T \quad (3)$$

$$\Sigma(t) = \Lambda(t) - m(t)[m(t)]^T \quad (4)$$

$$R(t) = [y(t) - m(t-1)]^T [\Sigma(t-1)]^{-1} [y(t) - m(t-1)] \quad (5)$$

Equation (2) in is an equation for calculating a mean vector m at a given time (t). The mean vector m provides an estimate of the mean for a time series of values. As shown in Equation (2), the mean vector m(t) is determined by blending the pattern vector y(t) with the mean vector for the prior time instance m(t-1). The blending of the pattern vector y(t) with the prior mean vector m(t-1) is performed by using a weighting factor μ to blend the two vectors. The weighting factor μ can be referred to as a memory parameter. As shown in Equation (2), increasing the value of memory parameter μ will increase the weight of the current pattern vector y(t) in the new mean vector m(t). The value of memory parameter μ provides a mathematical way to implicitly select the size of the memory window $W_m$ for the analysis without having to explicitly use all of the pattern window vectors within a window in the calculation of the mean vector. As the value of memory parameter μ decreases, the effective size of the memory window $W_m$ increases.

Equation (3) provides a method for determining a second moment Λ(t) at a given point in the time series of data. As shown in Equation (3), the second moment Λ(t) is also determined using the memory parameter μ to blend the eigenvalue (or sum of eigenvalues) for the current pattern vector y(t) with the second moment for the prior time Λ(t-1). It is noted that $[y(t)]^T$ refers to the transpose of the pattern vector. Equation (4) then provides a method for calculating the variance Σ(t) based on the second moment Λ(t) and the eigenvalue (or sum of eigenvalues) for m(t).

As measurement values or sampling values are accumulated for various time points "t", Equation (1) allows for generation of corresponding pattern window vectors y(t), while Equations (2), (3), and (4) allow for calculation of the mean m(t), second moment Λ(t), and variance Σ(t). Calculation of the mean and variance values then allows for determination of an additional "residue value" R(t), which is defined in Equation (5). As shown in Equation (5), the residue value R(t) corresponds to a difference between the current pattern vector y(t) and the mean vector for the previous pattern vectors m(t-1). In other words, the residue value R(t) provides a rough mathematical estimation of the amount of difference between a current pattern vector y(t) and the previous pattern vectors that have been blended together to form the mean vector.

The residue value R(t) can be used to identify potentially anomalies or outliers within the pattern vectors y. Instead of attempting to identify an individual time point t where an individual set of measured data points is anomalous, calculation of the residue value R(t) allows for determination of when a time series of measurement data points is anomalous relative to the prior patterns of the measured data points. An anomalous pattern vector at a time "t" can be identified based on determination of a conventional standard deviation (σ) for the series of residue values R(t) leading up to time "t". A threshold can then be set based on the calculated standard deviation for the residue values, such as having a threshold of 1σ, 2σ, 5σ, 10σ, or any other convenient value based on the standard deviation.

It is noted that for Equations (2)-(5), by using a memory parameter μ, the pattern window vectors within a memory window $W_m$ do not need to be explicitly retained and used in a calculation. Instead, only the current pattern window vector (at time t) and the vectors or values for the immediately preceding time "t-1" need to be retained in order to calculate the new analysis vectors or values at time "t". This simplifies the calculation as well as improving the speed of the calculation. If desired, the calculation of the mean vector, second moment, and variance in Equations (2)-(4) can be explicitly performed on all pattern vectors within a sampling window.

Application of Residue Calculation—Pipeline Corrosion Detection

Based on Equations (1)-(5), anomalies in time series of measurements can be identified based on patterns in the time series, as opposed to being based analysis of individual measured values. This can be useful, for example, in situations where an anomaly corresponds to a change in the sequence of measured values generated by a system, as opposed to an anomaly where the absolute magnitude of a measured value is unusual.

One application for using a residue calculation can be for determining a corrosion rate. The principle of operation is the change in resonant frequency of the fork as material is corroded from its prongs, which are exposed to the flow in the pipeline or other process equipment used in a refinery. However, absolute measurements of resonant frequencies are inherently noisy to make a measurement of a low corrosion rate in a short period of time. To compensate for this, a corrosion sensor that includes two mechanical oscillators can be used. The two oscillators can be (i) a non-corroding reference fork and (ii) a corroding sensing fork.

A comparative evaluation of the sensing fork and the reference fork is shown in FIG. 1. The y-axis in FIG. 1 corresponds to resonant frequency while the x-axis is time. In FIG. 1, each demarcation line on the x-axis corresponds to 30 days of measurements of the sensor in a refinery hydrocarbon stream. The bottom curve, corresponding to the sensing fork, shows a steady downward drift due to corrosion, while the top curve from the reference fork hold relatively steady except for fluctuations induced by operating conditions. It is noted in FIG. 1 that the sensing fork and the reference fork have substantially different resonant frequencies. This is due to the differences in construction of the two forks. In particular, the sensing fork includes a corrodible insert that serves as the corrodible portion of the sensing fork. The corrodible insert increases the overall length of the fork, resulting in a different resonant frequency for two forks with an otherwise similar shape.

Figure 2:
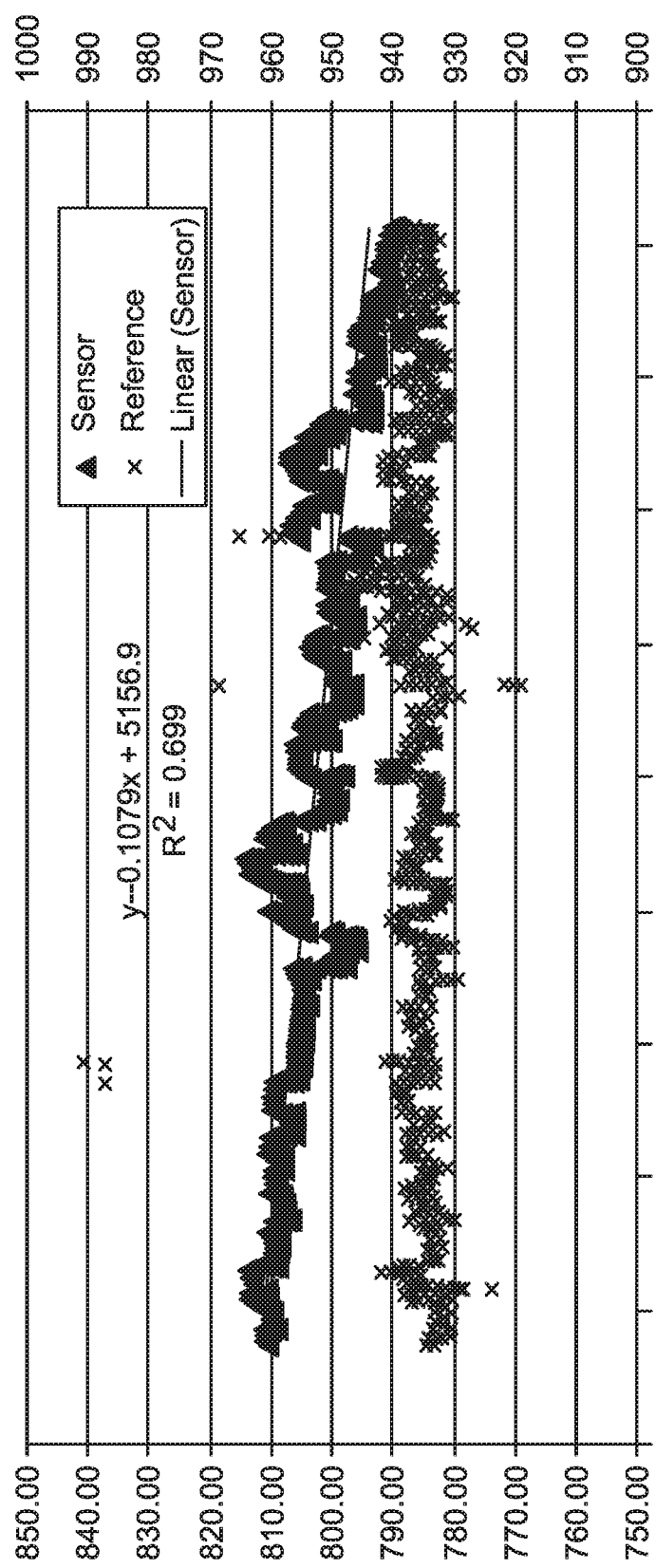

FIG. 2 shows the same data in FIG. 1, but replotted so that the data for the two forks is closer together. This allows a smaller scale to be used for the two y-axes in FIG. 2, so that the downward drift in resonant frequency for the sensing fork is more apparent. In FIG. 2, the top curve now corresponds to the sensing fork and corresponds to the left hand y-axis values. The reference fork data in the bottom curve corresponds to the right hand y-axis values. As shown in FIG. 2, although the data for the sensing fork shows a clear downward slope overall, corresponding to a reduction in resonant frequency over time, the data is also noisy with large fluctuations.

Figure 3:
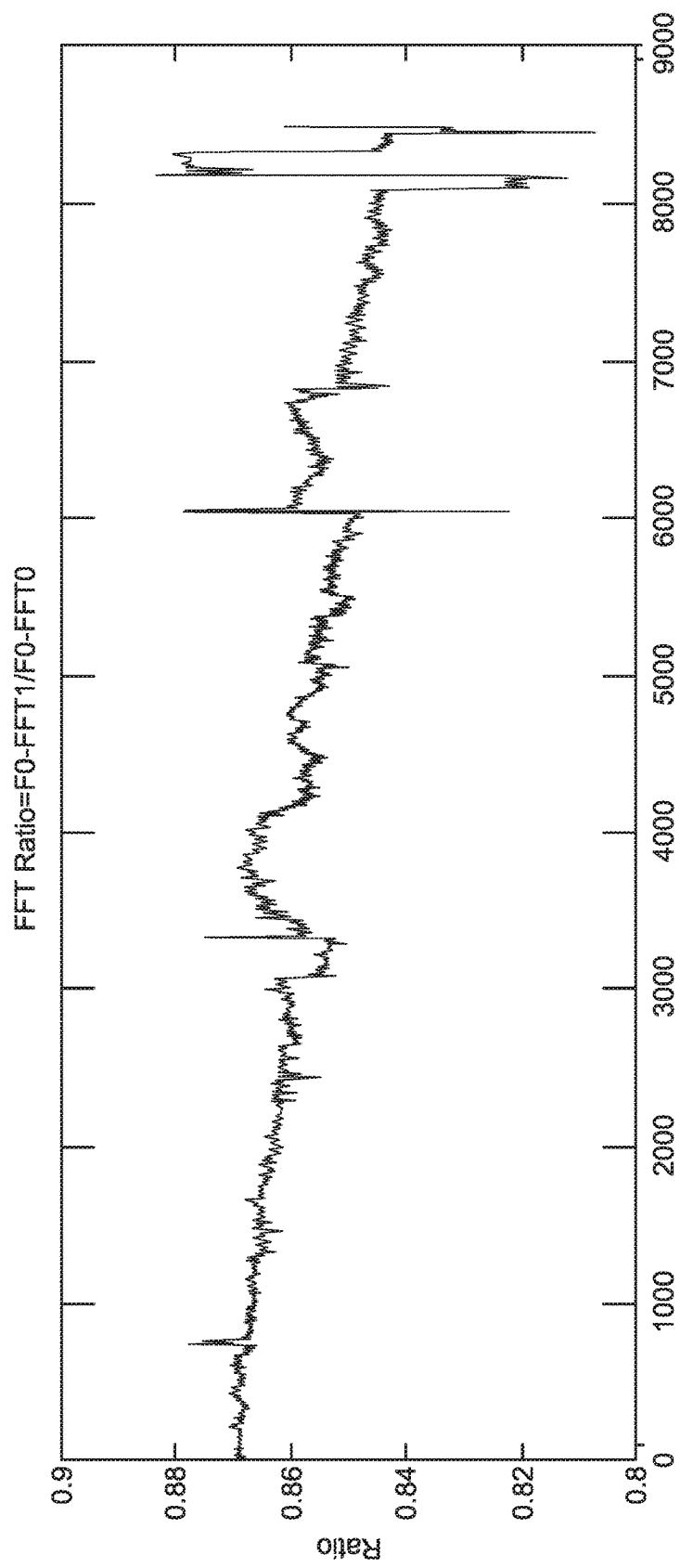

FIG. 3 shows an example of one method for attempting to use the reference fork to mitigate data fluctuations. FIG. 3 shows a plot of the ratio of the sensing fork data to the reference fork data. By plotting the ratio, changes in the fluid environment that impact both the sensing fork and the reference fork are somewhat accounted for. However, as shown in FIG. 3, substantial data fluctuations remain. In particular, FIG. 2 showed some short-lived variations in data that appeared in the data for either only the sensing fork or only the reference fork. Combining the sensing fork and reference fork data does not cure such variations encountered in the data for only one of the forks.

Figure 4:
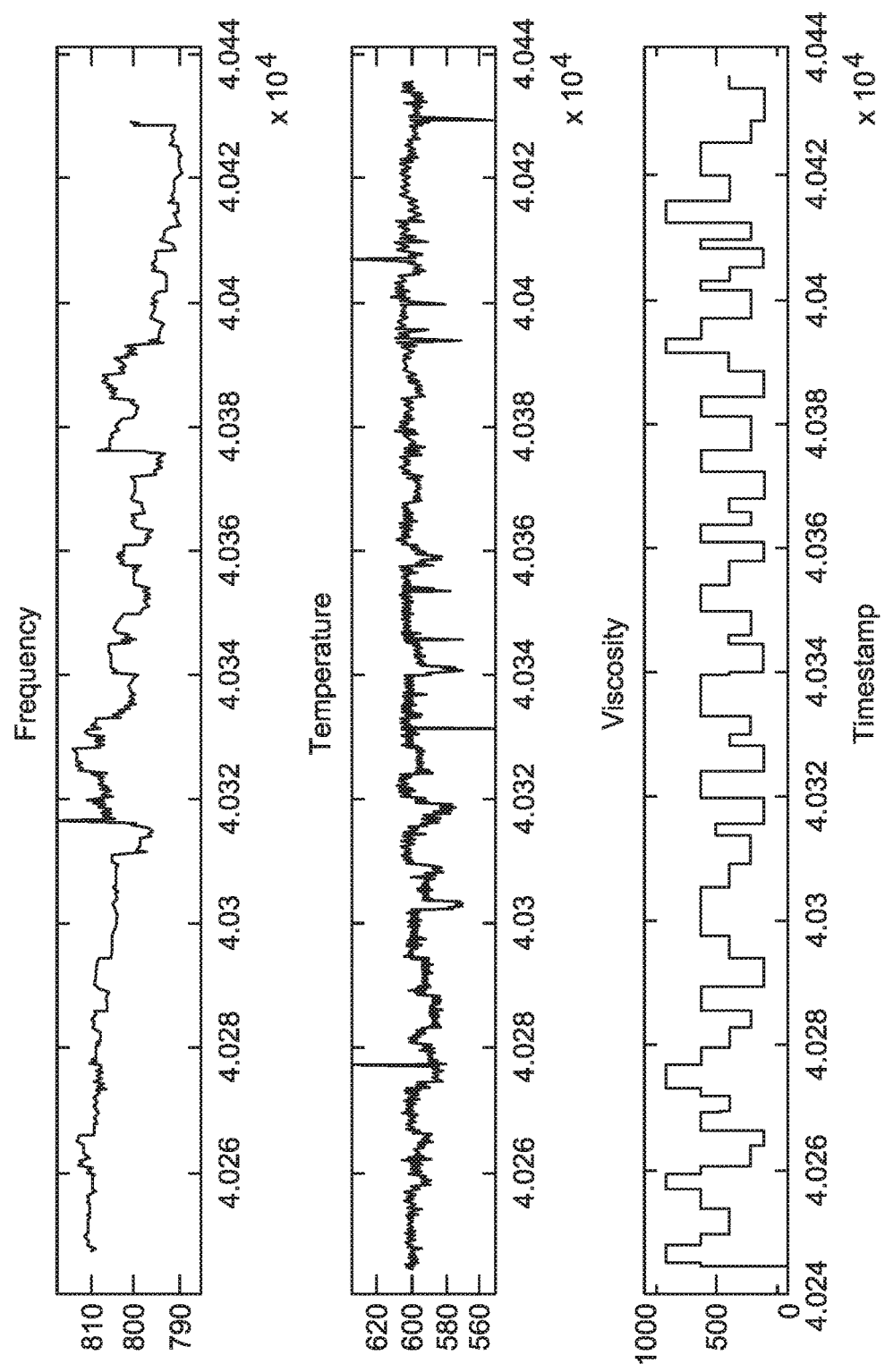

FIG. 4 depicts another potential conventional method to account for data fluctuations. In FIG. 4, the top plot shows the resonant frequency data from the sensing fork. The middle plot shows the corresponding temperature data for the process fluid at the same times, while the bottom plot shows the viscosity data for the process fluid. As shown in FIG. 4, there is no readily apparent correlation between changes in the frequency of the sensing fork and the temperature or viscosity of the fluid flow. While some of the sudden frequency changes correlate with temperature and viscosity changes, the actual relationships between these parameters and the frequency are not easily apparent from the data, and are also difficult to extract using analytical methods.

Instead of attempting to analyze the mechanical oscillator data by direct analysis of the measured values, analysis of pattern windows in time history data for the measured values can be used. As described above, pattern windows can be formed based on, for example, the ratio of resonant frequency data for the sensing and reference oscillators over time, and a residue value $R(t)$ can be calculated at each measurement (or sampling) point. Based on the variance in the calculated residue values, unusual patterns or anomalies can be detected in the patterns of the frequency data. Upon detection of an anomaly, the measured values corresponding to the anomaly can be excluded from the calculation of the corrosion or erosion rate.

The data in FIG. 3 represents a time series of measurements $x(t)$ from the forks. This time series of data can be analyzed using the measurements $x(t)$ to form pattern window vectors similar to equation (1) above. Equations (2)-(5) above can then be used to determine various quantities for the time series. For example, the mean vector $m(t)$ in equation (2) automatically provides a historical trend of the data in the recent past, and a simple linear regression of the mean vector provides a robust corrosion rate estimate automatically extracted as a by-product of the analysis above.

Figure 5:
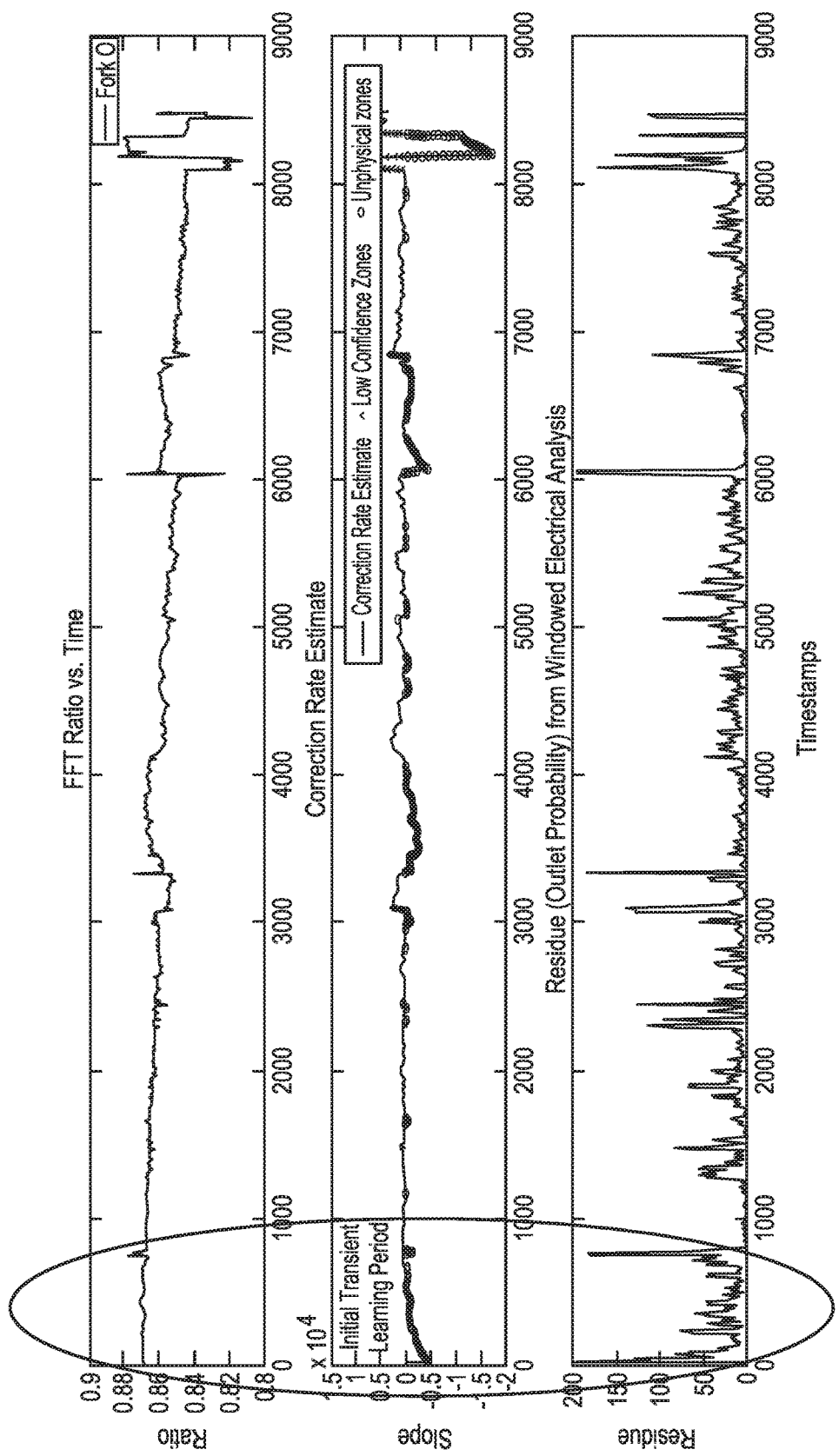

FIG. 5 illustrates the application of pattern window analysis on the data in FIG. 3. The top plot in FIG. 5 corresponds to the data shown in FIG. 3. It is shown again in FIG. 5 for convenience in comparing the time dependence of the data in FIG. 3 with the corrosion rate calculation shown in the middle plot and the residual value calculation shown in the bottom plot. It is noted that the corrosion rate calculation in the middle plot shows the negative of the slope of the mass of the oscillator versus time. This should be a plot that is greater than zero at most times, as a steady loss of mass over time would be a slope less than zero, so the negative of such a slope would be positive. The scale used in the middle plot may make the non-zero values harder to visualize, but the middle plot does in fact show non-zero values at most points in time. For the residual value calculation shown in the bottom plot in FIG. 5, equations (2)-(5) were applied using a pattern window size of 20, a $\mu$ of 0.01, and a threshold value of $5\sigma$. As shown in FIG. 5, the windowed statistical analysis method requires an initial "training period" when it learns the "normal" distribution of the data. Presence of abnormal events in this period could alter the results, but generally does not have a significant effect if most of the data in the training period is normal. Following the training period, the algorithm can be used to automatically produce the middle plot of the figure, which contains corrosion rate estimates as well as values flagged for being excludable as anomalies based on the windowed statistical analysis, and values flagged as unphysical due to corresponding to an increase in mass rather than a decrease (i.e. material accretion rather than corrosion). Such an output is convenient for an engineer or operator for fast and objective evaluation of equipment condition and subsequent maintenance planning.

In the bottom plot in FIG. 5, the early portion of the plot (prior to about 500 hours of measured data) represents a learning period for the residue function. As types of patterns exhibited by the ratio of resonant frequency measurements are incorporated into the mean vector in Equation (2), the resulting residue value $R(t)$ from Equation (5) becomes lower in value. After this learning period, the value of the residue $R(t)$ drops below the $1\sigma$ value for the residue and remains there. At this point, the residue $R(t)$ can be used for detection of anomalous patterns in the data.

In the bottom plot in FIG. 5, a $5\sigma$ threshold is used to identify sampling values as being anomalous. Using a different threshold can increase or decrease the number of events counted as anomalies, if a higher or lower sensitivity to unusual patterns is desired. More generally, any convenient multiple (or other mathematic manipulation) of the standard deviation $\sigma$ in the residue can be used to establish a threshold value for anomaly detection.

It is noted that the value of the residue $R(t)$ is not dependent on the absolute magnitude of the values in the raw data, such as the measured resonant frequency values. For example, near the 5000 hour time stamp, the bottom plot for the residue value shows a spike. This leads to identification of data that should be excluded when determining the corrosion rate of the sensor, as indicated by the highlighted values in the middle corrosion rate plot. However, the actual raw data in the top plot near the 5000 hour time stamp does not appear visually to be substantially different from the other surrounding data. This is an example of the ability of the windowed statistical analysis technique to identify patterns within a time series of data that are anomalous, even though the individual raw data values may appear reasonable.

In FIG. 5, only one residue plot is shown based on the measured resonant frequency data. Another potential advantage of calculation residue values is that multiple residue value plots can be generated by modifying the pattern window size and the memory factor $\mu$. For example, two residue plots could be used to identify two types of patterns within a data set. A first residue plot could be tuned to have a smaller pattern window, such as a pattern window of 5, and a higher value of $\mu$, such as $\mu=0.05$ or 0.1. This combination of pattern window size of memory factor $\mu$ would be suitable for more rapid identification of shorter time scale patterns. The residue value for this parameter selection may be more noisy, so a $2\sigma$ threshold could be appropriate for identifying anomalous patterns. The same initial measurement data could also be used for calculation of a second set of residue values with a larger pattern window, such as a window size of 20, and a lower value of $\mu$, such as $\mu=0.01$ or $\mu=0.005$. This second type of residue calculation will require a longer induction time. Additionally, due to the size of the pattern window, this second residue calculation will tend to take longer to identify an anomalous pattern. However, this second type of calculation will also be suitable for detecting patterns that require a longer window to observe. In general, using a larger pattern window size can reduce the amount of natural variation in the residue, so a smaller $1\sigma$ or $2.5\sigma$ threshold can be suitable for identifying an anomalous pattern. More generally, any convenient number of residues can be calculated based on a set of measurement values, in order to provide residues with different sensitivity to different types of pattern anomalies.

Additional Embodiments

Embodiment 1. A method for determining a corrosion-related value (such as a corrosion rate) for a sensor in a fluid flow in a corrosive or erosive environment, comprising: exciting a mechanical oscillator disposed in a fluid flow; monitoring the mechanical oscillator to obtain a plurality of sampling values at a plurality of times, a sampling value comprising at least one of a resonant frequency f and a quality factor Q; forming pattern window vectors having a first window size based on the plurality of sampling values, each pattern window vector being associated with a time from the plurality of times; determining residue values for the pattern window vectors at the plurality of times based on a mean vector and a variance, the mean vector and the variance for a pattern window vector associated with a time being based on at least a portion of the pattern window vectors; identifying one or more residue values greater than a threshold value; excluding sampling values from the plurality of sampling values that correspond to times associated with the one or more identified residue values; and determining a corrosion-related value based on sampling values from the plurality of sampling values that are different from the excluded sampling values.

Embodiment 2. A method for determining a corrosion-related value for a sensor in a fluid flow in a corrosive or erosive environment, comprising: exciting a mechanical oscillator disposed in a fluid flow; monitoring the mechanical oscillator to obtain a plurality of sampling values at a plurality of times, a sampling value comprising at least one of a resonant frequency f and a quality factor Q; forming pattern window vectors having a first window size based on the sampling values; selecting a memory value $\mu$, where $1/\mu$ is greater than the first window size; determining residue values for the pattern window vectors at the plurality of times based on the selected memory value, a moving mean vector, and a moving variance, the moving mean vector and the moving variance for a pattern vector associated with a time being based on at least a portion of the pattern window vectors; identifying one or more residue values greater than a threshold value; excluding sampling values from the plurality of sampling values that correspond to times associated with the one or more identified residue values; and determining a corrosion-related value based on sampling values from the plurality of sampling values that are different from the excluded sampling values.

Embodiment 3. The method of any of the above Embodiments, wherein a sampling value comprises both the resonant frequency and the quality factor.

Embodiment 4. The method of any of the above Embodiments, wherein monitoring the mechanical oscillator further comprises monitoring a reference oscillator disposed in the fluid flow to obtain a plurality of reference sampling values, the reference oscillator being resistant to corrosion in the fluid flow.

Embodiment 5. The method of Embodiment 4, wherein the reference oscillator is non-corrodible.

Embodiment 6. The method of Embodiment 4 or 5, wherein the plurality of reference sampling values are obtained at the plurality of times.

Embodiment 7. The method of any of Embodiments 4 to 6, further comprising excluding reference sampling values from the plurality of reference sampling values that correspond to times associated with the one or more identified residue values, wherein determining the corrosion-related value is further based on reference sampling values from the plurality of reference sampling values that are different from the excluded reference sampling values.

Embodiment 8. The method of Embodiment 7, wherein determining the corrosion-related value based on the sampling values and the reference sampling values comprises determining the corrosion-related value based on a ratio of the sampling values and the reference sampling values.

Embodiment 9. A method for determining a corrosion-related value for a sensor in a fluid flow in a corrosive or erosive environment, comprising: monitoring a corrosion sensor disposed in a fluid flow to obtain a plurality of sampling values at a plurality of times, a sampling value comprising one or more measured values of the monitored sensor; forming pattern window vectors having a first window size based on the plurality of sampling values, each pattern window vector being associated with a time from the plurality of times; determining residue values for the pattern window vectors at the plurality of times based on a mean vector and a variance, the mean vector and the variance for a pattern window vector associated with a time being based on at least a portion of the pattern window vectors; identifying one or more residue values greater than a threshold value; excluding sampling values from the plurality of sampling values that correspond to times associated with the one or more identified residue values; determining a change in at least one measured value of the monitored sensor based on sampling values from the plurality of sampling values that are different from the excluded sampling values; and determining a corrosion-related value based on the determined change in the at least one measured value.

Embodiment 10. A method for determining a corrosion rate for a sensor in a fluid flow in a corrosive or erosive environment, comprising: determining a change in at least one measured value of the monitored sensor based on sampling values from the plurality of sampling values that are different from the excluded sampling values; forming pattern window vectors having a first window size based on the sampling values; selecting a memory value µ, where 1/µ is greater than the first window size; determining residue values for the pattern window vectors at the plurality of times based on the selected memory value, a moving mean vector, and a moving variance, the moving mean vector and the moving variance for a pattern vector associated with a time being based on at least a portion of the pattern window vectors; identifying one or more residue values greater than a threshold value; excluding sampling values from the plurality of sampling values that correspond to times associated with the one or more identified residue values; determining a change in at least one measured value of the monitored sensor based on sampling values from the plurality of sampling values that are different from the excluded sampling values; and determining a corrosion-related value based on the determined change in the at least one measured value.

Embodiment 11. The method of Embodiments 9 or 10, wherein the monitored corrosion sensor comprises an electrical resistance probe, a mechanical oscillator, or a combination thereof.

Embodiment 12. The method of any of the above Embodiments, further comprising excluding one or more additional sampling values from the plurality of sampling values, the one or more additional sampling values having corresponding residue values lower than the threshold value.

Embodiment 13. The method of Embodiment 12, wherein the one or more additional excluded sampling values are excluded as sampling values corresponding to an increase in mass for the corrosion sensor.

Embodiment 14. The method of any of the above Embodiments, wherein determining a residue value comprises: determining a mean vector based on the pattern window vectors; calculating a variance for the pattern window vectors; and calculating the residue value based on the determined mean vector and the calculated variance.

Embodiment 15. The method of Embodiment 14, wherein the determined mean vector comprises a moving mean vector and the calculated variance comprises a moving variance.

Embodiment 16. The method of Embodiment 15, wherein a plurality of residue values are calculated based on each pattern window vector, each residue value calculation being based on a different memory value L for forming pattern window vectors.

Embodiment 17. The method of any of the above Embodiments, wherein the threshold value is selected based on a standard deviation of the determined residue values.

Embodiment 18. The method of any of the above Embodiments, wherein a plurality of pattern window vectors are formed based on each sampling value, at least two of the plurality of pattern window vectors having a different window size.

Embodiment 19. The method of any of the above Embodiments, wherein the mean vector and the variance for a pattern window associated with a time are based on pattern window vectors within a sampling window, the sampling window having a second window size, the second window size being larger than the first window size.

Embodiment 20. The method of any of the above Embodiments, wherein the corrosive or erosive environment includes a deposition environment.

Embodiment 21. The method of any of the above embodiments, wherein determining a corrosion-related value comprises: determining a resonant frequency decrease in the mechanical oscillator based on sampling values from the plurality of sampling values that are different from the excluded sampling values; and determining a corrosion rate based on the determined resonant frequency decrease.

The principles and modes of operation of this invention have been described above with reference to various exemplary and preferred embodiments. As understood by those of skill in the art, the overall invention, as defined by the claims, encompasses other preferred embodiments not specifically enumerated herein.

We claim:

1. A method for determining a corrosion-related value for a sensor in a fluid flow in a corrosive or erosive environment, comprising:

providing at least one mechanical oscillator and locating the at least one mechanical oscillator in the fluid flow, wherein the at least one mechanical oscillator including one of (i) a mechanical oscillator having two regions of differing corrosion resistance, wherein one of the two regions is a reference region that is resistant to corrosion in the fluid flow and another of the two regions is a non-resistant region that is not resistant to corrosion in the fluid flow, or (ii) a first mechanical oscillator having one corrosion resistance that is not resistant to corrosion in the fluid flow and a second reference mechanical oscillator having a different corrosion resistance that is resistant to corrosion in the fluid flow;

exciting the at least one mechanical oscillator disposed in the fluid flow;

monitoring the at least one mechanical oscillator to obtain a plurality of sampling values at a plurality of times from the non-resistant region or the first mechanical oscillator, a sampling value comprising at least one of a resonant frequency f and a quality factor Q, wherein the monitoring further includes obtaining a plurality of reference sampling values at the plurality of times from the reference region, or the second reference mechanical oscillator;

forming pattern window vectors having a first window size based on the plurality of sampling values, each pattern window vector being associated with a time from the plurality of times;

determining residue values for the pattern window vectors at the plurality of times based on a mean vector and a variance, the mean vector and the variance for a pattern window vector associated with a time being based on at least a portion of the pattern window vectors;

identifying one or more residue values greater than a threshold value;

excluding sampling values from the plurality of sampling values that correspond to times associated with the one or more identified residue values, wherein excluding sampling values further includes excluding reference sampling values from the plurality of reference sampling values that correspond to times associated with the one or more identified residue values; and determining a corrosion-related value based on sampling values from the plurality of sampling values that are different from the excluded sampling values and reference sampling values from the plurality of reference sampling values that are different from the excluded reference sampling values, wherein determining the corrosion-related value based on the sampling values and the reference sampling values comprises determining the corrosion-related value based on a ratio of the sampling values and the reference sampling values.

2. The method of claim 1, wherein determining a corrosion-related value comprises:
determining a resonant frequency decrease in the at least one mechanical oscillator based on sampling values from the plurality of sampling values that are different from the excluded sampling values; and
determining a corrosion rate based on the determined resonant frequency decrease.

3. The method of claim 1, further comprising excluding one or more additional sampling values from the plurality of sampling values, the one or more additional sampling values having corresponding residue values lower than the threshold value.

4. The method of claim 3, wherein the one or more additional excluded sampling values are excluded as sampling values corresponding to an increase in mass for the corrosion sensor.

5. The method of claim 1, wherein determining a residue value comprises:
determining a mean vector based on the pattern window vectors;
calculating a variance for the pattern window vectors; and
calculating the residue value based on the determined mean vector and the calculated variance.

6. The method of claim 5, wherein the determined mean vector comprises a moving mean vector and the calculated variance comprises a moving variance.

7. The method of claim 6, wherein a plurality of residue values are calculated based on each pattern window vector, each residue value calculation being based on a different memory value $\mu$ for forming pattern window vectors.

8. The method of claim 1, wherein the threshold value is selected based on a standard deviation of the determined residue values.

9. The method of claim 1, wherein a plurality of pattern window vectors are formed based on each sampling value, at least two of the plurality of pattern window vectors having a different window size.

10. The method of claim 1, wherein the mean vector and the variance for a pattern window associated with a time are based on pattern window vectors within a sampling window, the sampling window having a second window size, the second window size being larger than the first window size.

11. The method of claim 1, wherein the corrosive or erosive environment includes a deposition environment.

12. The method of claim 1, wherein a sampling value comprises both the resonant frequency and the quality factor.

13. The method according to claim 1, further comprising:
selecting a memory value $\mu$, where $1/\mu$ is greater than the first window size,
wherein determining residue values comprising determining residue values for the pattern window vectors at the plurality of times based on the selected memory value, a moving mean vector, and a moving variance, the moving mean vector and the moving variance for a pattern vector associated with a time being based on at least a portion of the pattern window vectors.

* * * * *